United States Patent [19]

Gutman

[11] 3,960,951
[45] June 1, 1976

[54] CERTAIN OXIME ESTERS

[75] Inventor: Arnold D. Gutman, Berkeley, Calif.

[73] Assignee: Stauffer Chemical Company, Westport, Conn.

[22] Filed: Aug. 5, 1974

[21] Appl. No.: 494,932

Related U.S. Application Data

[63] Continuation of Ser. No. 275,601, July 27, 1972, abandoned, which is a continuation of Ser. No. 882,336, Dec. 4, 1969, abandoned, which is a continuation-in-part of Ser. No. 649,024, June 26, 1967, abandoned.

[52] U.S. Cl. .......................... 260/566 AC; 71/121; 424/327
[51] Int. Cl.² ...................................... C07C 131/00
[58] Field of Search ........................... 260/566 AC

[56] References Cited
FOREIGN PATENTS OR APPLICATIONS 825,709  10/1969  Canada ...................... 260/566 AC Primary Examiner—Gerald A. Schwartz
Attorney, Agent, or Firm—Edwin H. Baker

[57] ABSTRACT

Compounds having the formula

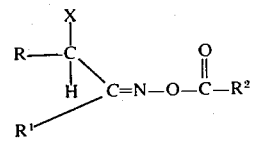

in which X is chlorine or bromine, R is hydrogen or alkyl having from 1 to 6 carbon atoms; $R^1$ is alkyl having 1 to 4 carbon atoms or haloalkyl having from 1 to 4 carbon atoms; phenyl or nuclear substituted derivatives thereof in which the substituents are halogen, nitro or lower alkyl, $R^2$ is alkyl having from 1 to 6 carbon atoms or haloalkyl having from 1 to 6 carbon atoms. The compounds are useful in controlling weeds and for inhibiting the growth of bacteria and fungi.

2 Claims, No Drawings

CERTAIN OXIME ESTERS

This application is a continuation of application Ser. No. 275,601, filed July 27, 1972, which is a continuation of application Ser. No. 882,336, filed Dec. 4, 1969, which is a continuation-in-part of application Ser. No. 649,024, filed June 26, 1967 all of which are now abandoned.

This invention relates to novel chemical compounds and to their use as herbicides and in controlling fungi and bacteria. More particularly, the chemical compounds are certain keto oxime esters.

The compounds of the present invention are those having the formula

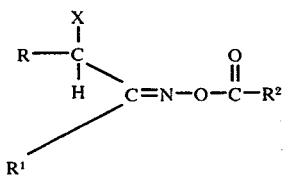

in which X is chlorine or bromine, preferably chlorine; R is hydrogen or alkyl having from 1 to 6 carbon atoms, preferably hydrogen; $R^1$ is alkyl having 1 to 4 carbon atoms, haloalkyl having from 1 to 4 carbon atoms, phenyl, or nuclear substituted derivatives thereof in which the substituents are halogen, nitro and lower alkyl, preferably chloromethyl; $R^2$ is alkyl having from 1 to 6 carbon atoms; haloalkyl having from 1 to 6 carbon atoms, preferably chloroalkyl having from 1 to 4 carbon atoms.

The compounds of the present invention are phytotoxic and are particularly useful as herbicides especially in post emergent control of weeds. The compounds are also useful in inhibiting the growth of bacteria and fungi and in inhibiting the growth of fungi upon cellulosic materials.

The compounds of the present invention can be prepared by reacting a compound of the formula

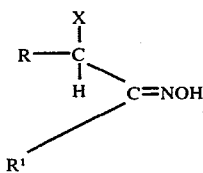

in which X, R and $R^1$ are as defined with a compound of the formula

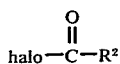

in which halo is chlorine or bromine and $R^2$ is as defined.

Preferably, the reaction is carried out in the presence of a base such as pyridine and in a solvent for the reactants. Generally, the reaction is exothermic so no heating is required. Cooling is sometimes required to control the reaction rate. The compounds of this invention can be recovered from the mixture and purified by standard procedures.

Compounds of the formula

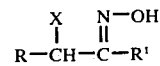

can be prepared by reacting

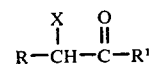

with excess hydroxylamine hydrochloride or hydroxylamine hydrobromide in ethanol and water, wherein X, R and $R^1$ are as defined. The reaction can be run with heating under reflux for several hours. The desired product is recovered and purified by conventional techniques.

Preparation of the compounds of this invention is illustrated by the following examples.

EXAMPLE 1

1,3-dichloroacetoneoxime 63.5 gms. (0.50 moles) 1,3-dichloropropanone, 69.5 gms. (1.00 moles) hydroxylamine hydrochloride, 250 ml. ethanol and 25 ml. of water were combined and heated under reflux for four hours. The cooled mixture was poured into 500 ml. of water. The aqueous solution was extracted with 3 – 100 ml. portions of chloroform. The chloroform phases were combined and dried with anhydrous $MgSO_4$. The chloroform was evaporated to give 66.3 g. (93.6% of theory) of 1,3-dichloroacetoneoxime,

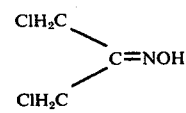

$N_D^{30} = 1.5044.$

EXAMPLE 2

1,3-dichloroacetoneoxime trichloroacetate 7.1 grams (0.05 moles) 1,3-dichloroacetoneoxime, 9.1 grams (0.05 moles) trichloroacetyl chloride and 100 ml. benzene were added to a 500 ml. flask, stirred and cooled to 10°C with an ice bath. 4.7 grams (0.06 moles) pyridine was added at a rate sufficient to maintain the reaction temperature below 20°C. After the addition of the pyridine, the ice bath was removed, and the mixture was stirred at room temperature for 1 hour. An additional 100 ml. benzene was added, and the mixture was washed with 50 ml. dilute HCl followed by two 100 ml. water washes. The benzene phase was dried with $MgSO_4$ and evaporated to give 10.4 grams 1,3-dichloroacetoneoxime trichloroacetate

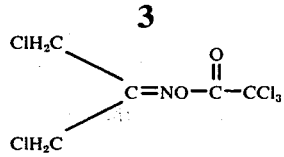

$N_D^{30} = 1.5078$.

The following is a table of certain selected compounds that have been prepared according to the procedure described hereto. Compound numbers have been assigned to each compound and are used throughout the remainder of the application.

TABLE 1

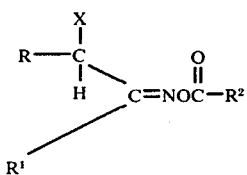

| Compound Number | R | R¹ | R² | X |
|---|---|---|---|---|
| 1 | hydrogen | chloromethyl | trichloromethyl | Cl |
| 2 | hydrogen | chloromethyl | bromomethyl | Cl |
| 3 | ethyl | ethyl | bromomethyl | Cl |
| 4 | propyl | methyl | bromomethyl | Cl |

The following tests illustrate utility of the compounds as herbicides and in controlling fungi and bacteria.

As previously mentioned, the herein described novel compositions produced in the above described manner are phytotoxic compounds which are useful and valuable in controlling various plant species. The compounds of this invention were tested as herbicides in the following manner.

Pre-emergence Herbicide Test

The seeds of crab grass foxtail, watergrass, red oats, pigweed, mustard and curled dock were planted in individual rows one-half inch deep in Santa Cruz sandy loam soil contained in compressed paper flats. Enough seeds were planted to give about thirty to fifty plants each of the weed species in each flat. The flats were watered after planting. The following day each flat was sprayed at the rate of 20 pounds of the candidate compound under test in 80 gallons of solution per acre. An atomizer was used to spray the solution on the soil surface. Two weeks later the degree of weed control was determined by comparing the amount of germination and growth of each weed in the treated flats with the weeds in several untreated control flats. The results of the pre-emergence herbicide test showed that compound 1 is especially useful in contolling crabgrass, foxtail, watergrass, red oats, pigweed, mustard and curled dock.

Post-emergence Herbicide Test

The seeds of crabgrass, watergrass, red oats, Indian mustard, curled dock and pinto beans were planted in individual rows in Santa Cruz sandy loam soil as described in the pre-emergence test. After growing for two weeks under greenhouse conditions, the plants were four to six inches tall. Thereafter, the candidate test compound was applied to the foliage by means of an overhead spray while the flat moved under the spray on a moving table. A concentration of 0.5% of active compound in the spray was used at a rate equivalent to approximately 20 pounds per acre. Two weeks after treatment, the injury results were recorded using a similar rating system as used in the pre-emergence test. Table II lists the results obtained therefrom.

TABLE II

| | Post-Emergence Activity Rate 20 Pounds Per Acre | | | | | |
|---|---|---|---|---|---|---|
| Compound Number | Crab-grass | Water grass | Red oats | Indian mustard | Curled dock | Pinto bean |
| 1 | +++ | +++ | +++ | +++ | +++ | +++ |
| 2 | − | − | + | +++ | − | +++ |
| 3 | ++ | + | + | +++ | +++ | +++ |
| 4 | ++ | + | + | +++ | + | +++ |

+++ = severe injury or death
++ = moderate injury
+ = slight injury
− = no injury The compounds of the present invention find particular utility as post-emergence herbicides and may be applied in a variety of ways at various concentrations. They may be combined with suitable carriers and applied as dusts, sprays or drenches. The amount applied will depend upon the nature of the weeds or plants to be controlled and the rate of application may vary from 1 to 80 pounds per acre. One particularly advantageous way of applying the compounds is as a narrow band along a row crop, straddling the row.

In vitro vial test

This test measures the bactericidal and fungicidal properties of a compound when in contact with a growing bacterium or fungus. The test is conducted by partially filling two 1-ounce vials with malt broth and one 1-ounce vial with nutrient broth. Next the test compound is added to the vials at a certain concentration, expressed in parts per million, and mixed with the broth. A water suspension of spores of the desired fungi or cells of the desired bacteria (one organism per vial) is added. The vials are then sealed and incubated for one week; at this time the vials are examined and the results recorded. Table IV shows the results of various compounds tested by the in vitro vial test.

TABLE IV

| | Concentration (p.p.m.) which inhibited growth | | | |
|---|---|---|---|---|
| | Fungus | | Bacteria | |
| Compound | Aspergillus niger | Penicillium sp. | Escherichia coli | Stapylococcus Aureus |
| 1 | >50 | (50) | >50 | 25 |
| 2 | 50 | (25) | >50 | 50 |
| 3 | 50 | 25 | >50 | 50 |
| 4 | >50 | 25 | >50 | 50 |

As can be seen by the test results the compounds of the present invention find particular utility as bactericides and fungicides. The compounds can be applied in a variety of ways at various concentrations. They can be combined with suitable carriers and applied as dusts, sprays or drenches. The amount applied will depend on the nature of the utility. The rate of application can also vary with the microbiological use intended.

I claim:

1. A compound having the formula

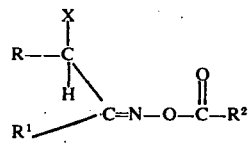

in which X is chlorine; R is hydrogen; $R^1$ is chloromethyl; $R^2$ is alkyl having from 1 to 6 carbon atoms.

2. The compound having the formula

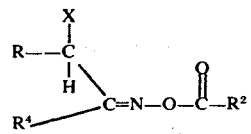

in which X is chloro; R is hydrogen; $R^1$ is chloromethyl; and $R^2$ is trichloromethyl.

* * * * *